United States Patent
Longo et al.

(10) Patent No.: US 10,675,300 B2
(45) Date of Patent: Jun. 9, 2020

(54) GROUP 3 METAL COMPOUNDS AND USE THEREOF IN THE TREATMENT OF SOLID TUMORS

(71) Applicant: UNIVERSITÀ DEGLI STUDI DI SALERNO, Fisciano SA (IT)

(72) Inventors: Pasquale Longo, Capaccio SA (IT); Carmela Saturnino, Montoro AV (IT); Claudio Arra, Bacoli NA (IT); Giuseppe Palma, Salerno SA (IT); Angelamaria Caporale, Castelvetere sul Calore AV (IT); Annaluisa Mariconda, Baronissi SA (IT); Maria Stefania Sinicropi, Rende CS (IT); Francesco Puoci, Cosenza CS (IT)

(73) Assignee: UNIVERSITÀ DEGLI STUDI DI SALERNO, Fisciano SA (IT)

( * ) Notice: Subject to any disclaimer, the term of this patent is extended or adjusted under 35 U.S.C. 154(b) by 0 days.

(21) Appl. No.: 16/099,065

(22) PCT Filed: May 5, 2017

(86) PCT No.: PCT/IB2017/052624
§ 371 (c)(1),
(2) Date: Nov. 5, 2018

(87) PCT Pub. No.: WO2017/191607
PCT Pub. Date: Sep. 11, 2017

(65) Prior Publication Data
US 2019/0240254 A1 Aug. 8, 2019

(30) Foreign Application Priority Data
May 5, 2016 (IT) .................. 102016000046245

(51) Int. Cl.
*C07F 17/00* (2006.01)
*A61K 31/28* (2006.01)
*A61P 35/00* (2006.01)
*A61K 33/24* (2019.01)

(52) U.S. Cl.
CPC .............. *A61K 33/24* (2013.01); *A61K 31/28* (2013.01); *A61P 35/00* (2018.01); *C07F 17/00* (2013.01)

(58) Field of Classification Search
CPC .................. C07F 17/00; A61K 31/28
See application file for complete search history.

(56) References Cited

PUBLICATIONS

Caporale et al. "Synthesis and Antitumor Activity of New Group 3 Metallocene Complexes" Molecules, Vole 22, Article 526, pp. 1-13.*
Sweeney et al., "Novel benzyl substituted titanocene anti-cancer drugs," *Journal of Organometallic Chemistry* 690:4537-4544, Elsevier B.V., (2005).
Bulls et al., "Relative Bond Dissociation Energies for Early Transition Metal Alkyl, Aryl, Alkynyl and Hydride Compounds, Equilibration of Metallated Cyclopentadienyl Derivatives of Peralkylated Hafnocene and Scandocene with Hydrocarbons and Dihydrogen," *Polyhedron* 7:1409-1428, Pergamon Press plc (1988).
Database CAPLUS, Chemical Abstract Service, XP-002765497, Accession No. 2004:497498 (2004).
Caporale et al., "Synthesis and Antitumor Activity of New Group 3 Metallocene Complexes," *Molecules* 22:Article 526, pp. 1-13 (2017).
International Search Report and Written Opinion of the International Searching Authority for PCT/IB2017/052624, European Patent Office, dated Aug. 29, 2017.

* cited by examiner

*Primary Examiner* — Joseph R Kosack
(74) *Attorney, Agent, or Firm* — Sterne, Kessler, Goldstein & Fox P.L.L.C.

(57) ABSTRACT

The present invention relates to the compounds of Formula 1

Formula 1 wherein M is Sc or Y,
Hal is Cl, Br, F or I
R is alkyl with 1-4 atoms of C
X is Cl, Br, F or I or a group such as that shown hereinafter

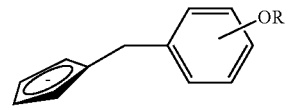

wherein R is alkyl with 1-4 atoms of C
and the use thereof in the treatment of solid tumors.

18 Claims, 2 Drawing Sheets

GROUP 3 METAL COMPOUNDS AND USE THEREOF IN THE TREATMENT OF SOLID TUMORS

The present invention relates to the compounds of Formula 1

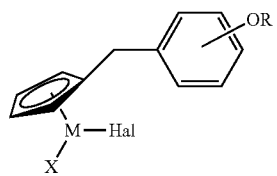

Formula 1 wherein M is Sc or Y,
Hal is Cl, Br, F or I
R is alkyl with 1-4 atoms of C
X is Cl, Br, F or I or a group such as that shown hereinafter

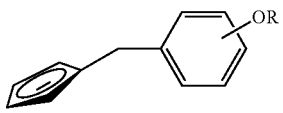

Wherein R is alkyl with 1-4 atoms of C
and the use thereof in the treatment of solid tumors.

In particular, the synthesis, the chemical characterization of new organometallic compounds of group 3 and the use thereof as antitumor agents are described, with particular reference to the topic application for the treatment of still not curable solid tumors, such as the triple negative breast cancer (TN) and the prostate cancer. The results deriving from these studies have led to the development of a new therapeutic approach for the pharmacological treatment of the TN breast cancer. In this way mastectomy can be avoided and the toxic aspects shown by the drugs currently used for these kinds of tumors can be reduced considerably.

STATE OF ART

The organo-metallic complexes (example: cis-platin, carbo-platin, etc.), which are nowadays available on the market, are substantially alkylating agents. The cisplatin enters the cells by diffusion wherein it is then converted into its active form. The species which are currently considered active are not determined with great certainty. It is believed that the active species is the monohydrate one, however the most common species is the dihydrate form. The main function of the cisplatin is to link to DNA. In fact, although the cisplatin is capable of interacting with several types of vital proteins for the DNA replication and the cell division, the main target remains DNA. However, such compound has considerable toxicity and several side effects. A main one is nephrotoxicity. Cisplatin, in fact, can cause renal damages (tubular degeneration, necrosis and mineralization of the tubular epithelial cells). Another effect is ototoxicity which above all appears in children.

Ototoxicity leads to the loss of equilibrium due to auditory difficulties. The initial symptoms include tinkling (ringing in the ears). These effects should stop at the end of the treatment, but sometimes it happens that some patients loose their hearing irreversibly in the range of high frequencies (>4 KHz). The other toxic symptoms are common to those caused by other antitumor drugs: nausea, vomiting, decrease in the red blood cells, tingling sensation in hands and feet: drug neurotoxicity, especially shown with high doses.

The decrease in platelets, face swellings, dyspnea (shortness of breath), muscle cramps, blurred vision and appetite loss are instead less common. Nausea and vomiting usually appear one hour after the drug administration and they can last for several hours.

Another drug particularly important in the oncology clinical therapy is represented by Doxorubicin which is one of the most effective antitumor agents for the treatment of leukaemia and a wide range of solid tumors$_{(1,9)}$. This compound belongs to the family of anthracyclines, thereamong there are other three molecules, one thereof already on the market for some time: Daunorubicin and other two drugs, already in clinical phase thanks to their antitumor effects: Epirubicin and Idarubicin. All of them have in common the 4-ringed 7,8,9,10-tetrahydrotetracene-5,12-quinone polycycle, but they differ for the residues R1, R2 and R3$_{(9)}$, as shown in the following formula.

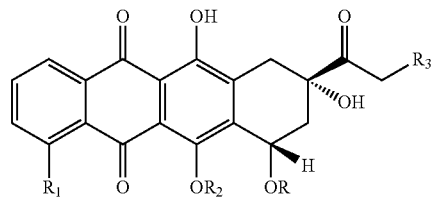

The whole family of anthracyclines shows cardiac toxicity, which can be fatal to the patient.

A crucial aspect in the oncology research is represented by the decrease in toxicity and selectivity focussed on cancerous cells only.

The present invention aims at the therapy of two among the neoplastic pathologies very widespread within the population: breast cancer (in particular TN) and prostate cancer, cancers for which the current oncotherapy is not effective, it is very toxic, often it cannot be applied.

Now it has surprisingly been found that with the pharmaceutical/pharmaco-technological approach which was performed, that is by implementing new molecules, which can be obtained with few synthetic steps, which are capable of inhibiting the tumor growth, it was possible to overcome the disadvantages of the state of art. Currently, with new rapid synthetic methods, new molecules were implemented, which were studied in vitro. The cytotoxic action of such new molecules on the two solid tumors taken into consideration was determined. The in-vitro studies allowed us to determine even DL50.

DESCRIPTION OF THE INVENTION

The present invention relates to the compounds of Formula 1

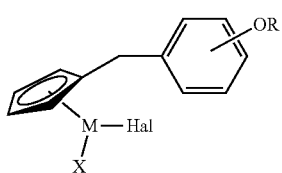

Formula 1 wherein M is Sc or Y,
Hal is Cl, Br, F or I
R is alkyl with 1-4 atoms of C
X is Cl, Br, F or I or a group of the following Formula 2

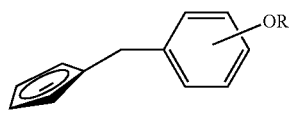

Formula 2 wherein R is alkyl with 1-4 atoms of C
a process for the production thereof and the use thereof as medicaments in particular in the treatment of solid tumors. In particular new organo-metallic derivatives of scandium and yttrium with cyclopentadienylic binders having substituted aromatic groups with methoxyl, the synthesis thereof and the pharmacological application thereof are described.

BRIEF DESCRIPTION OF THE FIGURES

Two figures are enclosed to the present description, showing

Preferred compounds have the following structures

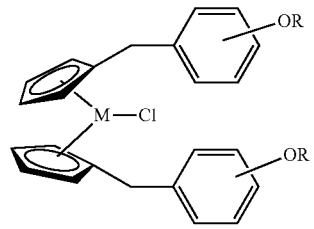

Formula 3

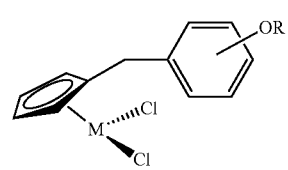

Formula 4 wherein M and R have the above-illustrated meanings.

Particularly preferred compounds have the following structures

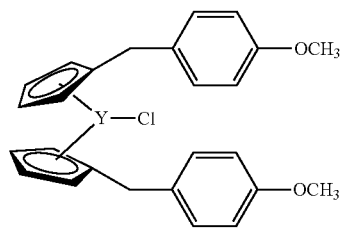

CAM-2

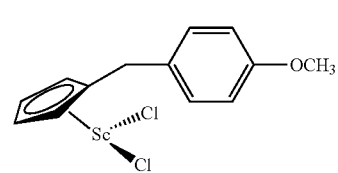

CAM-3

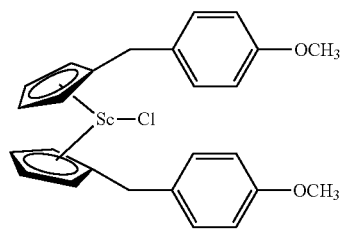

CAM-4

The synthesis of the new scandium- and yttrium-based metallorganic complexes was performed by reaction between lithium salt of the suitable binder and the metal halide. The binder was obtained by reaction between the cyclopentadiene (obtained by retro Diels-Alder of dicyclopentadiene) and the suitable aromatic aldehyde to give 6-aryl-fulvene which was reduced and salified by the lithium superhydride. In the following scheme (Scheme 1) the performed synthesis process is shown.

Scheme 1

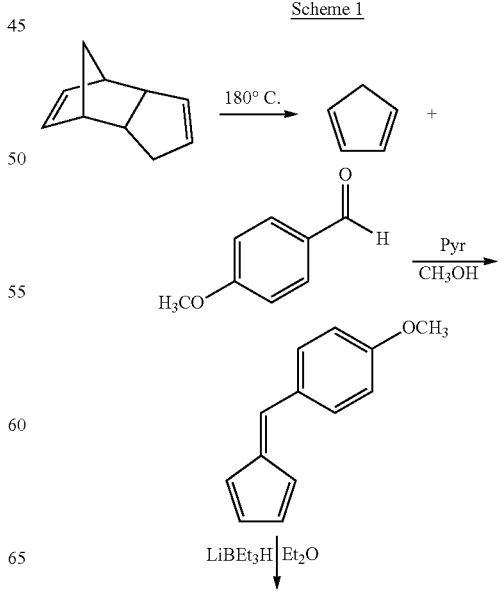

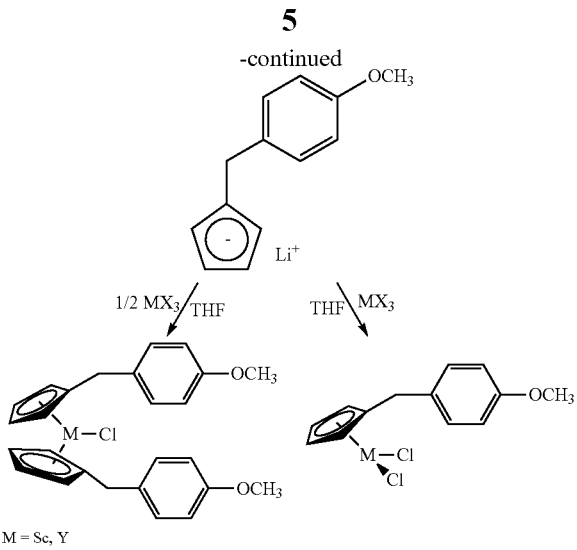

M = Sc, Y

The evaluation of the biological activity of the synthesized molecules allowed to show that they have a considerable effectiveness in the inhibition of the two solid tumors taken into consideration by us. The effectiveness of such molecules depends upon the chemical structure of the same. These compounds, then, in reality, can represent a new class of organo-metallic molecules provided with antiproliferative activity. The experiments performed on cell cultures of triple negative breast cancers (MDA.MB213) and prostate cancers (DU145) allowed to establish that the cell growth inhibition, obtained with some of the new synthesized molecules, can be related to antiblastic activity, to depending concentrations with a Lethal Dose 50 (DL50) with low concentrations (5 µM).

Figure 1:
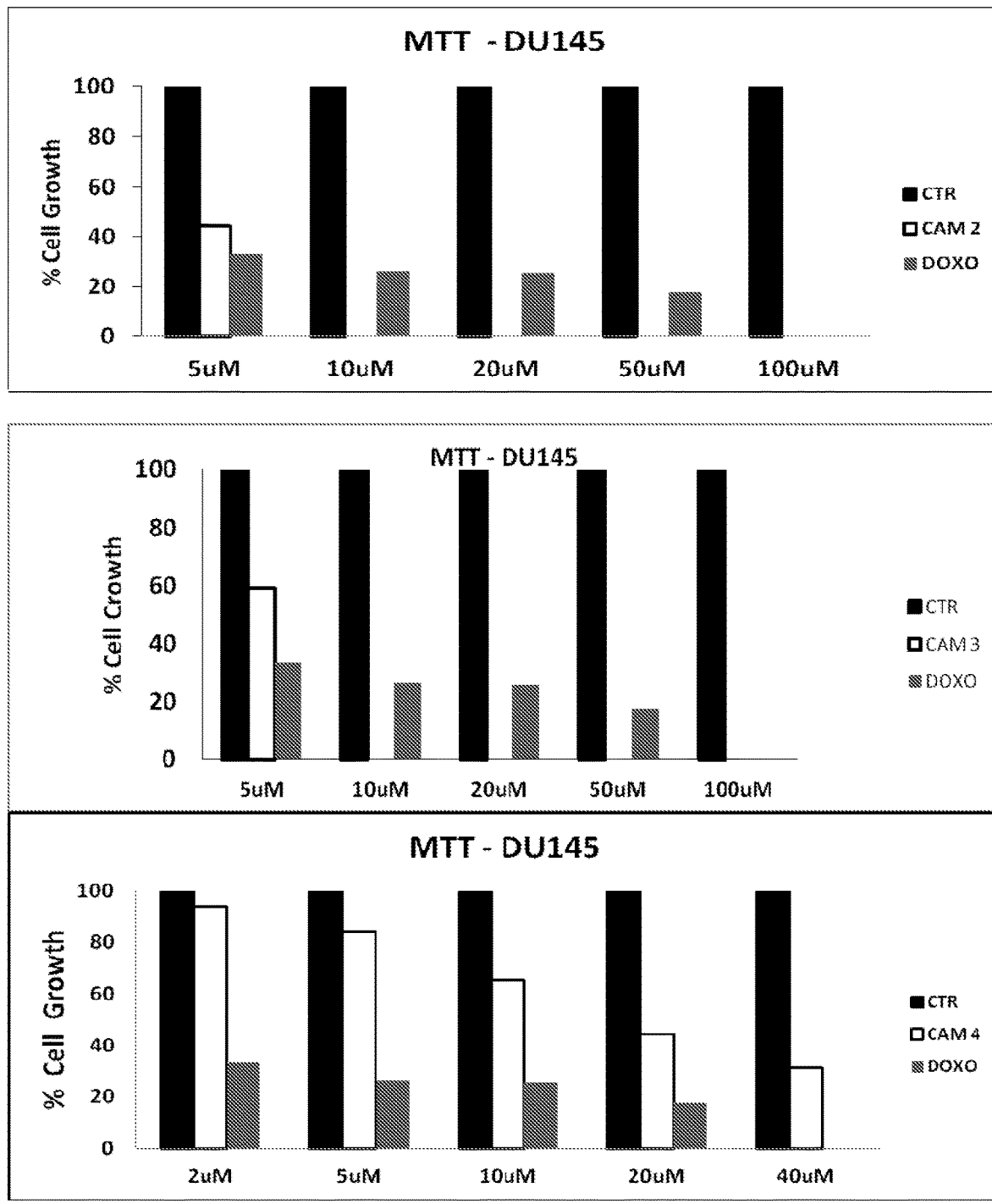
FIG. 1 the evaluation of the inhibitory activity of CAM2 (a), CAM3 (b) and CAM4 (c) on the cell growth of DU145 cells in presence of different concentrations, determined by MTT assay. The cell viability was expressed as percentage of proliferated cells with respect to the cells treated with the different compounds and the same cells used as control and FIG. 2 the evaluation of the inhibitory activity of CAM2 (a), CAM3 (b) and CAM4 (c) on the cell growth of MDA.MB231 cells in presence of different concentrations, determined by MTT assay. The cell viability was expressed as percentage of proliferated cells with respect to the cells treated with the different compounds and the same cells used as control.
Figure 2:
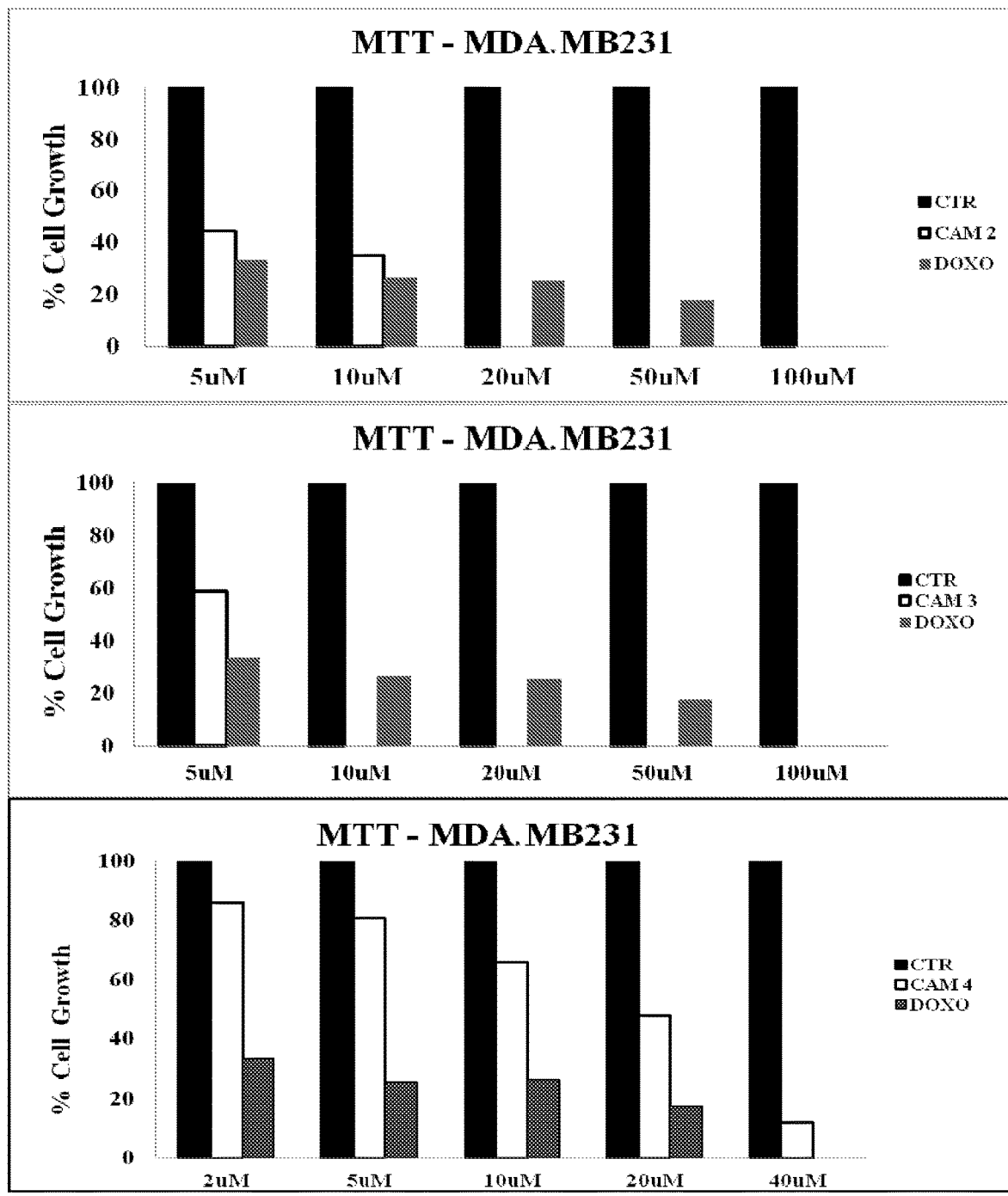

Hereinafter the structures of the synthesized metallorganic compounds are shown and FIGS. 1 and 2 show the results of the biological tests.

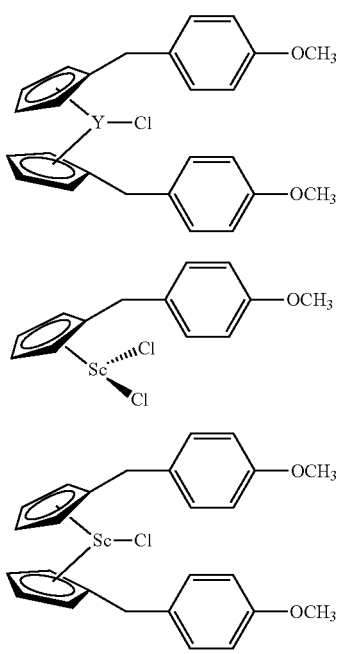

CAM-2

CAM-3

CAM-4

By way of illustration and not with limitative purposes examples of synthesis of the new complexes and of the cytotoxic activity thereof are described hereinafter.

Example 1

Synthesis of the complexes. It provided 4 reaction steps.
Retro Diels-Alder reaction of Dicyclopentadiene to form Cyclopentadiene. (Scheme The reaction apparatus comprises a 250-ml three-necked flask whereon a dropping funnel and a bulb condenser are assembled. A Claisen head is positioned on the condenser, which head is connected to a condenser wherein running water circulates, to this latter condenser a caudate pipe is connected, wherein the distilled cyclopentadiene is collected.

The reaction flask is placed into an isomantle and positioned on a stirring plate.

The flask is half filled-in with decalin, whereas dicyclopentadiene is placed into the dropping funnel. One works in inert atmosphere. As soon as decalin starts boiling, reaching the temperature of 180° C., one makes dicyclopentadiene to drop into the flask. At the temperature of 180° C. dicyclopentadiene is subjected to retro Diels-Alder and it is transformed into the monomer, the vapours thereof flow in the Claisen head and are condensed in a cooled-down collection pipe.

Reaction of cyclopentadiene with 4-methoxy-benzaldehyde to form 6-p-methoxy-phenyl-fulvene. (see scheme 1)

The reaction is performed in inert atmosphere. 30 ml of anhydrous methanol, 4.1 ml of Cyclopentadiene and 2.4 ml of 4-methoxybenzaldeide are put into a a caudate flask. The reaction starts by adding 2.5 ml of the pyrrolidine base. The solution colour changes immediately from transparent to red-orange. After about 20 minutes a red precipitate is formed. The reaction is followed by means of chromatography on TLC by using an eluent mixture constituted by ethyl acetate/dichloromethane (7:3). When TLC shows one single spot the reaction is interrupted by adding 1.8 ml of acetic acid. The reaction work-up is performed by extraction by adding 10 ml of ethyl ether and 10 ml of distilled water. After having transferred the mixture in a separating funnel and after having separated the two phases, the aqueous phase is washed 3 times with 30 ml of ethyl ether. The organic phases are re-united and washed with a concentrated solution of NaCl. The organic phase is treated with anhydrous $Na_2SO_4$. At last, it is filtered and dried.

Reduction of fulvene to form the corresponding lithium salts.

The reaction, performed in anhydrous diethyl ether at room temperature, as reducing agent uses $LiB(Et)_3H$, also known as super-hydride. It provides the nucleophilic addition of one hydride to the double bond 5-6 of fulvene, by using $LiB(Et)_3H$ as donor of equivalent reducing agents, a slight excess is used compared to the stoichiometric of super-hydride: fulvene/super-hydride of 1:1,2. (see scheme 1) The selection of $LiB(Et)_3H$ as reducing agent derives from its high selectivity. In fact, the double bond 5-6 of fulvene has a high polarity due to the inductive effect of the methoxylic group linked to benzene; this increase in polarity allows the reducing agent to attack selectively the double bond 5-6 and not the dienic component of fulvene. The super-hydride is available on the market in THF molar solution 1, then, before use, it has to be dried.

Reduction of 4-methoxyphenylfulvene.

In inert atmosphere 6.5 ml of superhydride solution are collected and transferred into a 250-ml caudate flask, the solvent (THF) is dried and the obtained solid white is dissolved in 70 ml of anhydrous ethyl ether. 1.0 g of 4-methoxyphenyl-fulvene are dissolved in 30 ml of anhydrous ethyl ether and they are added to the solution of the reducing agent. It is left under the nitrogen flow, at room temperature, for one night and a suspension is formed. The reaction mixture is transferred in a caudate pipe wherein the lithium salt is left to precipitate. The solvent is removed by piping and the precipitate is washed with 50 ml of anhydrous ethyl ether. The salt is dried and weighed.

The formation of mono and bi-substituted complexes takes place after reaction with binder with $ScCl_3$ or $YCl_3$. For the synthesis of the monosubstituted complexes a THF solution of the binder is made to drop in an equimolar solution of THF of the metal at a temperature of −78° C., whereas for the formation of the bi-substituted complex, it is suitable to make the solution of THF of the metal to drop on that of the binder. The reaction conditions remain unchanged except for the stoichiometric ratios. In this case, in fact, the metal moles are halved (binder:metal=1:½). The reaction is performed at a temperature of −78° C., by means of an ethanol bath, cooled with solid $CO_2$.

Example 2

Synthesis of the complex $[Cp-CH_2—C_6H_5—OCH_3]_2YCl$. (CAM2)

In dry-box, in two distinct flasks, 200 mg of salt of 4-methoxybenzyl-cyclopentedienyl of lithium and 101 mg of $YCl_3$ are weighed. The binder is solubilized with 8 ml of anhydrous THF and the solution is transferred into the dropping funnel. The metal halid is solubilized in 16 ml of anhydrous THF and transferred into the reaction flask. The flask is dipped into the bath thermostated at −78° C., then the binder is slowly added into the solution containing the metal halide. It is left under stirring for one night by making the temperature to rise slowly until room temperature. The solvent is dried and the obtained solid product is solubilized in 40 ml of anhydrous dichloromethane, it is filtered on celite to remove the lithium chloride. The solvent is dried and the caudate pipe is brought in dry box for the subsequent sample recovery and weighing procedures. The product was characterized by means of protonic NMR assay, mass spectrometry and elementary analysis.

$^1H$ NMR (d ppm, $CDCl_3$, 300 MHz): 2.81 [d, 4H, $C_5H_4—CH_2—C_6H_4—OCH_3$], 2.93 [d, 4H, $C_5H_4—CH_2—C_6H_4—OCH_3$], 3.60 [s, 4H, $C_5H_4—CH_2—C_6H_4—OCH_3$], 3.71 [s, 6H, $C_5H_4—CH_2—C_6H_4—OCH_3$], 5.99 [s, 2H, $C_5H_4—CH_2—CH_4—OCH_3$], 6.09 [s, 2H, $C_5H_4—CH_2—C_6H_4—OCH_3$], 6.21 [s, 2H, $C_5H_4—CH_2—C_6H_4—OCH_3$], 6.38 [s, 2H, $C_5H_4—CH_2—C_6H_4—OCH_3$], 6.84 [m, 4H, $C_5H_4—CH_2—C_6H_4—OCH_3$], 7.10 [m, 4H, $C_5H_4—CH_2—C_6H_4—OCH_3$].

Mass data: 377.1 [M-Na$^+$—$C_6H_4OCH_3$ e-Cl], 355 [M$^+$-$C_6H_4OCH_3$ e-Cl], 307 [M$^+$-$C_5H_4CH_2C_6H_4OCH_3$], Elementary analysis: Calculated for $C_{26}H_{26}O_2ClY$ (%) C, 63.1; H, 5.3; Cl, 7.2. found C, 62.9; H, 5.1; Cl, 7.3

Example 3

Synthesis of $[Cp-CH_2—C_6H_5—OCH_3)]ScCl_2$. (CAM3)

In dry-box, in two distinct flasks, 200 mg of the salt of 4-methoxybenzyl-cyclopentedienyl of lithium and 157 mg of $ScCl_3$ are weighed. The binder is solubilized with 8 ml of anhydrous THF and the solution is transferred into the dropping funnel. The metal halide is solubilized in 32 ml of anhydrous THF and transferred into the reaction flask. The flask is dipped into the bath thermostated at −78° C., then the binder is slowly added into the solution containing the metal halide. It is left under stirring for one night by making the temperature to rise slowly until room temperature. The solvent is dried and the obtained solid product is solubilized in 40 ml of anhydrous dichloromethane, it is filtered on celite to remove the lithium chloride. The solvent is dried and the caudate pipe is brought in dry box for the subsequent sample recovery and weighing procedures.

The product was characterized by means of protonic NMR analysis, mass spectrometry and elementary analysis.

$^1H$ NMR (d ppm, $CDCl_3$, 300 MHz): 2.80 [d, 2H, $C_5H_4—CH_2—C_6H_4—OCH_3$], 2.92 [d, 2H, $C_5H_4—CH_2—C_6H_4—OCH_3$], 3.60 [s, 3H, $C_5H_4—CH_2—C_6H_4—OCH_3$], 5.98 [s, 1H, $C_5H_4CH_2—C_6H_4—OCH_3$], 6.09 [s, 1H, $C_5H_4—CH_2—C_6H_4—OCH_3$], 6.23 [d, 1H, $C_5H_4—CH_2—CH_4—OCH_3$], 6.37 [m, 1H, $C_5H_4—CH_2—C_6H_4—OCH_3$], 6.84 [m, 2H, $C_5H_4—CH_2—C_6H_4—OCH_3$], 7.05 [m, 2H, $C_5H_4—CH_2—C_6H_4—OCH_3$].

Mass data: (the complex appears in dimeric form) 403 [$M_2$-Na$^+$—($C_6H_4OCH_3$) e-Cl], 373.2 [$M_2$-Na$^+$—($CH_4OCH_3)_2$], 321 [$M^{30}$-($C_6H_4OCH_3)_2$ e-2Cl]

Elementary analysis: Calculated for $C_{13}H_{13}OCl_2Sc$ (%) C, 51.8; H, 4.3 Cl, 23.6. found C, 51.6; H, 4.1; Cl, 23.8.

Example 4

Synthesis of the complex $[Cp-CH_2—C_6H_5—OCH_3]_2ScCl$. (CAM4)

In dry-box, in two distinct flasks, 150 mg of the salt of 4-methoxybenzyl-cyclopentedienyl of lithium and 59 mg of $ScCl_3$ are weighed. The binder is solubilized with 4 ml of anhydrous THF and the solution is transferred into the dropping funnel. The metal halide is solubilized in 8 ml of anhydrous THF and transferred into the reaction flask. The flask is dipped into the bath thermostated at −78° C., then the binder is added slowly into the solution containing metal halide. It is left under stirring for one night by making the temperature to rise slowly until room temperature. The solvent is dried and the obtained solid product is solubilized in 40 ml of anhydrous dichloromethane, it is filtered on celite to remove the lithium chloride. The solvent is dried and the caudate pipe is brought in dry box for the subsequent sample weighing procedures.

The product was characterized by means of protonic NMR analysis, mass spectrometry and elementary analysis.

$^1H$ NMR (d ppm, $CDCl_3$, 300 MHz): 3.00 [s, 4H, $C_5H_4—CH_2—CH_4—OCH_3$], 3.12 [s, 4H. $C_5H_4—CH_2—C_6H_4—OCH_3$], 3.79 [s, 4H, $C_5H_4—CH_2—C_6H_4—OCH_3$], 3.83 [s, 4H, $C_5H_4—CH_2—C_6H_4—OCH_3$] 3.94 [s, 6H, $C_5H_4—CH_2—C_6H_4—OCH_3$], 6.14 [s, 2H, $C_5H_4—CH_2—C_6H_4—OCH_3$], 6.28 [s, 2H, $C_5H_4—CH_2—C_6H_4—OCH_3$], 6.39 [s, 2H, $C_5H_4—CH—C_5H_4—OCH_3$], 6.55 [s, 2H, $C_5H_4—CH_2—C_6H_4—OCH_3$], 6.55 [m, 4H, $C_5H_4—CH_2—C_6H_4—OCH_3$], 6.98 [m, 4H, $C_5H_4—CH_2—C_6H_4—OCH_3$].

Mass data: 382.2 [M-K$^+$—$CH_4OCH_3$], 377.2 [M$^+$-2Cl], 343 [M$^+$-$C_5H_4CH_2C_6H_4OCH_3$], Elementary analysis: Calculated for $C_{26}H_{26}O_2ClSc$ (%) C, 69.2; H, 5.8; Cl, 7.9. found C, 69.4; H, 5.6; Cl, 8.0

Example 5 Biological Test

CAM2 (compound acronym) was assayed to check the inhibition activity thereof on human tumor cells of (not hormone-depending—FIG. 2a) prostate cancer and on cell lines of Triple Negative breast cancer (lack in the expression of the receptors of estrogens, of progesterone and of HER2—FIG. 3a).

The subject compound shows cell growth inhibition activity depending upon concentration. At concentrations of 20 µM the growth inhibition is stronger (95%), whereas at concentrations of 5 µM it is weaker (58%) The compound shows an activity of DL50 at low concentrations (<5 µM).

At last, we can state that the compound under study shows an activity of inhibiting the tumor cell growth, related to antiblastic activity.

Materials

MDA.MB213—Human cell line of breast cancer acquired by ATCC (American Tissue Cell Colture—ATCC® HTB-26™), triple negative for ER receptor DU145—Human cell line of prostate cancer acquired by ATCC (American Tissue Cell Colture—ATCC® HTB-81™)

MTT Cell Proliferation Assay Kit—Purchased by TREVIGEN—Catalog #4890-025-K

Methods

The compound was dissolved in a solution of DMSO concentrated at 100%, therefrom the dilutions programmed according to the scheme shown in figure A and B are obtained and in 96-multiwell plates $2 \times 10^4$ cells are deposited (plated).

After 24 hours the compounds under study in contact with the cells at the pre-established concentrations are used, in order to determine the lethal dose 50, that is the dose thereat there is 50% of cell growth inhibition.

After 48 hours of exposition to our compound, the growth inhibition effect is determined by means of a colorimetric assay.

The MTT assay is a measurement of sensitivity of cell proliferation based upon the decrease in the salt of tetrazolium, 3, [4,5-dimethyithiazol-2-]-2,5-diphenyl-bromide-tetrazolium (MTT).

Changes in the cell proliferative activity caused by our compounds can be quantified with MTT. MTT is reduced to an insoluble colouring agent, by the mitochondrial enzymes associated to the metabolic activity. MTT reduction is mainly due to the glycolytic activity inside the cell associated to the presence of NADH and NADPH.

CAM 3

CAM3 (compound acronym) was assayed to check the inhibition activity thereof on human tumor cells of (not hormone-depending—FIG. 2b) prostate cancer and on cell lines of Triple Negative breast cancer (lack in expression of the receptors of estrogens, of progesterone and of HER2—FIG. 3b).

The subject compound shows cell growth inhibition activity depending upon concentration. At higher concentrations (10 µM) the growth inhibition is very strong (95%), whereas at lower concentrations it is weaker (40%)

The compound shows an activity of DL50 at low concentrations (5/10 uM). At last, we can state that the compound under study shows a strong activity of inhibiting the tumor cell growth, related to antiblastic activity.

Materials

MDA.MB213—Human cell line of breast cancer acquired by ATCC (American Tissue Cell Colture—ATCC® HTB-26™), triple negative for ER receptor DU145—Human cell line of prostate cancer acquired by ATCC (American Tissue Cell Colture—ATCC® HTB-81™)

MTT Cell Proliferation Assay Kit—Purchased by TREVIGEN—Catalog #4890-025-K

Methods

The compound was dissolved in a solution of DMSO concentrated at 100%, therefrom the dilutions programmed according to the scheme shown in figure A and B are obtained, and in 96-multiwell plates $2 \times 10^4$ cells are deposited (plated).

After 24 hours the compounds under study in contact with the cells at pre-established concentrations are used, in order to determine the lethal dose 50, that is the dose thereat there is 50% of cell growth inhibition.

After 48 hours of exposition to our compound, the growth inhibition effect is determined by means of a colorimetric assay.

The MTT assay is a measurement of cell proliferation sensitivity based upon the reduction in the salt of tetrazolium, 3, [4,5-dimethylthiazol-2-]-2,5-diphenyl bromide-tetrazolium (MTT). Changes in the cell proliferative activity caused by our compounds can be quantified with MTT. MTT is reduced to an insoluble colouring agent, by the mitochondrial enzymes associated to the metabolic activity. MTT reduction is mainly due to the glycolytic activity inside the cell associated to the presence of NADH and NADPH.

CAM 4

CAM4 (compound acronym) was assayed to check the inhibition activity thereof on human tumor cell lines of (not hormone-depending—FIG. 2c) prostate cancer and on cell lines of Triple Negative breast cancer (lack in the expression of the receptors of estrogens, of progesterone and of HER2—FIG. 3c).

The subject compound shows cell growth inhibition activity depending upon concentration. At higher concentrations (40 µM) the growth inhibition is stronger (88%), whereas at lower concentrations (5 µM) the inhibition is very low (14%).

The compound shows an activity of DL50 at low concentrations (20 uM).

From the graphs we exclude that the compound activity can add to that of the solvent. At last we can state that the compound under study shows a strong tumor cell growth inhibition, related to antiblastic activity.

Materials

MDA.MB213—Human cell line of breast cancer acquired by ATCC (American Tissue Cell Colture—ATCC® HTB-26™), triple negative for ER receptor DU145—Human cell line of prostate cancer acquired by ATCC (American Tissue Cell Colture—ATCC® HTB-81™)

MTT Cell Proliferation Assay Kit—Purchased by TREVIGEN—Catalog #4890-025-K

Methods

The compound was dissolved in a solution of DMSO concentrated at 100%, therefrom the dilutions programmed according to the scheme shown in A e B are obtained, in 96-multiwell plates $2 \times 10^4$ cells are deposited (plated).

After 24 hours the compounds under study in contact with the cells at the pre-established concentrations are used, in order to determine the lethal dose 50, that is the dose thereat there is 50% of cell growth inhibition.

After 48 hours of exposition to our compound, the growth inhibition effect is determined by means of a colorimetric assay.

MTT assay is a measurement of the cell proliferation sensitivity based upon the reduction in the salt of tetrazolium, 3, [4,5-dimethylthiazol-2-]-2,5-diphenyl bromide-tetrazolium (MTT). Changes in the cell proliferative activity caused by our compounds can be quantified with MTT. MTT is reduced to an insoluble colouring agent, by the mitochondrial enzymes associated to the metabolic activity. MTT reduction is mainly due to the glycolytic activity inside the cell associated to the presence of NADH and NADPH.

The invention claimed is:

1. A compound of Formula I:

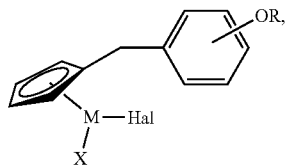

Formula 1 wherein:
M is Sc or Y;
Hal is Cl, Br, F or I;
R is alkyl with 1-4 carbon atoms;
X is Cl, Br, F, I, or a group of Formula 2:

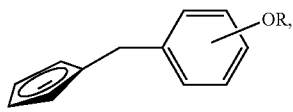

Formula 2 wherein R is alkyl with 1-4 carbon atoms.

2. The compound according to claim 1 having Formula 3:

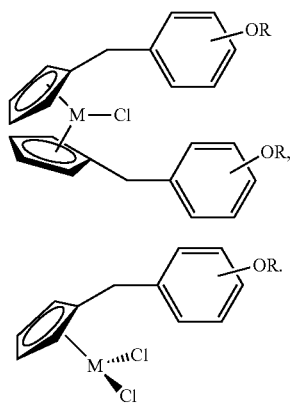

Formula 3

Formula 4

3. The compound according to claim 1 selected from the group consisting of:

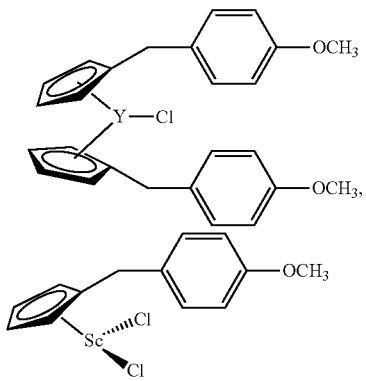

and

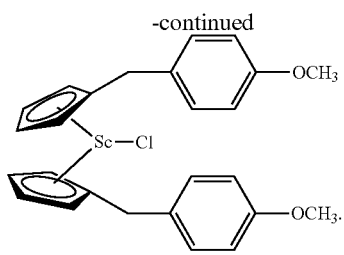

4. A method of treating tumors in a subject, the method comprising administering to the subject a compound according to claim 1.

5. A process for the production of the compound according to claim 1, the process comprising:
   i) a retro Diels-Alder reaction of dicyclopentadiene to form cyclopentadiene at a temperature of about 180° C. in decalin;
   ii) reaction of cyclopentadiene with methoxy-benzaldehyde to form 6-methoxy-phenyl-fulvene in the presence of pyrrolidine as a base;
   iii) reduction of 6-methoxy-phenyl-fulvene to form the corresponding lithium salt, using $LiB(Et)_3H$; and
   iv) formation of the compound of claim 1 by reaction of the lithium salt of iii) with the required stoichiometric amount of $ScCl_3$ or $YCl_3$ at a temperature of −78° C.

6. The compound according to claim 2 having Formula 3:

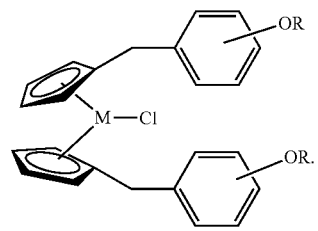

Formula 3

7. The compound according to claim 2 having Formula 4:

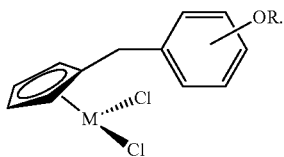

Formula 4

8. The compound of claim 3 which is:

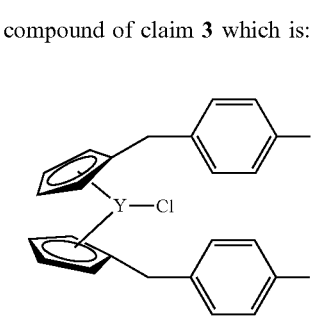

9. The compound of claim 3 which is:

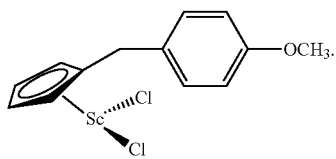

10. The compound of claim 3 which is:

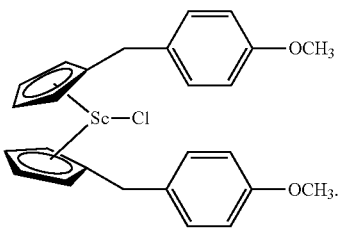

11. The method of claim 4, wherein the tumor is a solid tumor.

12. A method of treating triple negative breast cancer or prostate cancer in a subject, the method comprising administered to the subject a compound according to claim 1.

13. A method of treating tumors in a subject, the method comprising administering to the subject a compound according to claim 8.

14. A method of treating tumors in a subject, the method comprising administering to the subject a compound according to claim 9.

15. A method of treating tumors in a subject, the method comprising administering to the subject a compound according to claim 10.

16. A method of treating triple negative breast cancer or prostate cancer in a subject, the method comprising administered to the subject a compound according to claim 8.

17. A method of treating triple negative breast cancer or prostate cancer in a subject, the method comprising administered to the subject a compound according to claim 9.

18. A method of treating triple negative breast cancer or prostate cancer in a subject, the method comprising administered to the subject a compound according to claim 10.

* * * * *